US00PP11664P

United States Patent [19]

Noodelijk

[11] Patent Number: Plant 11,664

[45] Date of Patent: Dec. 5, 2000

[54] CHRYSANTHEMUM PLANT NAMED 'RED REFOCUS'

[75] Inventor: Robert Noodelijk, Woubrugge, Netherlands

[73] Assignee: Chrysanthemum Breeders Association N.V., Netherlands

[21] Appl. No.: 09/149,460

[22] Filed: Sep. 9, 1998

[51] Int. Cl.[7] ..... A01H 5/00

[52] U.S. Cl. ..... Plt./298

[58] Field of Search ..... Plt./298

[56] References Cited

PUBLICATIONS

UPOU–ROM, Feb. 1999, Plant Variety Database, GTI Jouve Retrieval Software, 2 citations for 'Red Refocus'.

*Primary Examiner*—Howard J. Locker

[57] ABSTRACT

A chrysanthemum plant named 'Red Refocus' characterized by its small sized blooms with red ray florets and green-yellow disc florets.

2 Drawing Sheets

The present invention is related to the plants in the following co-pending applications:

| Application no. | Filing Date | Title |
|---|---|---|
| 09/149,300 | 09/09/98 | Refocus |
| 09/149,299 | 09/09/98 | Pink Refocus |
| 09/149,657 | 09/09/98 | White Refocus |

BACKGROUND OF THE INVENTION

The present invention comprises a new a distinct cultivar of chrysanthemum plant that is a natural occurring sport of a parent chrysanthemum named Refocus. Parent chrysanthemum Refocus is also described in this application. The new cultivar was discovered as a whole plant mutation in May, 1993 by Rob Noodelijk in a greenhouse in Ter Aar, Holland.

The first act of asexual reproduction of Red Refocus was accomplished when vegetative cuttings were taken from the initial selection in August 1993 in a controlled environment in Ter Aar, Holland.

SUMMARY OF THE INVENTION

The present invention is a new and distinct variety of chrysanthemum bearing small sized blooms with red ray florets and green-yellow disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
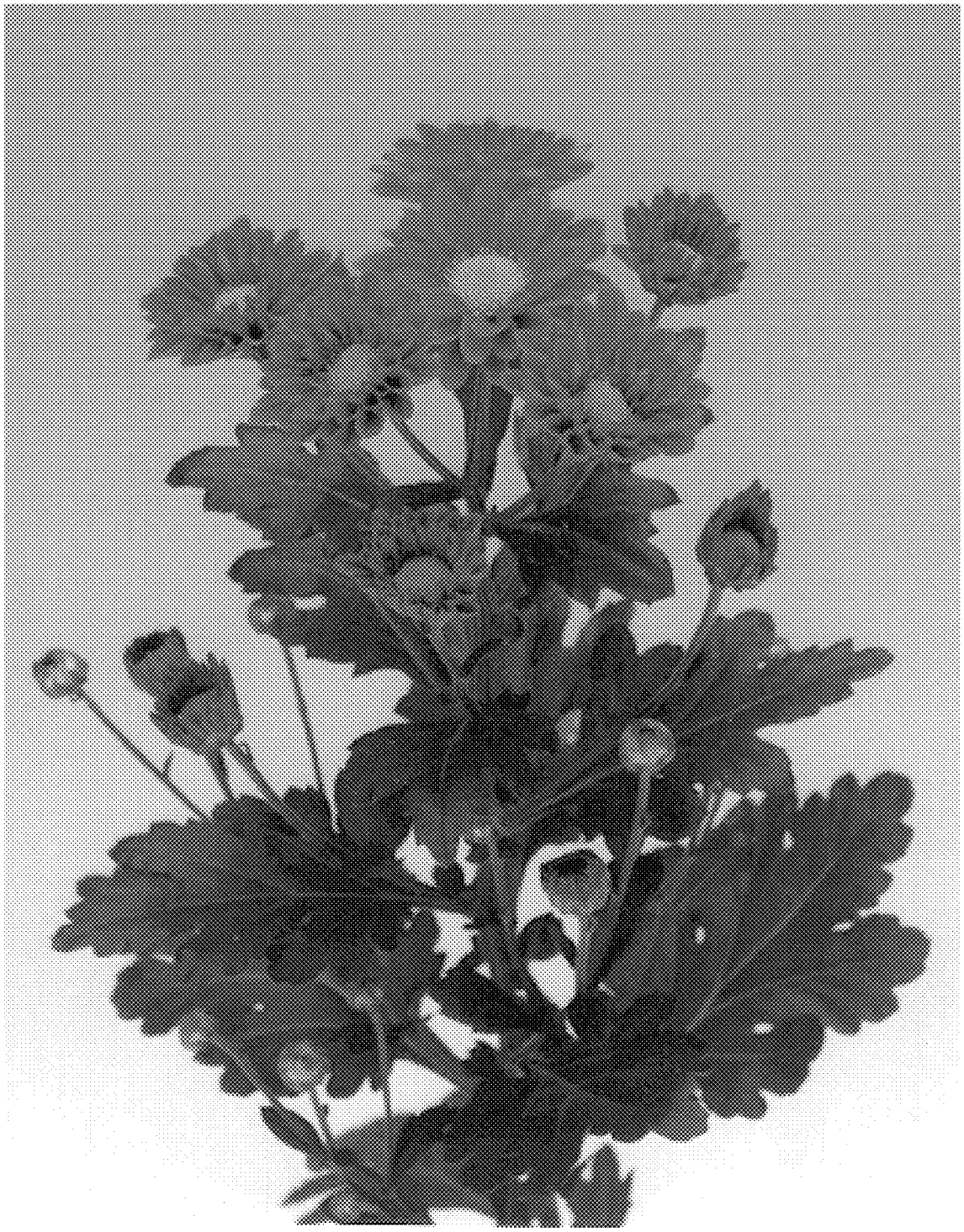
FIG. 1 shows the stem of the cultivar in full bloom.
Figure 2:
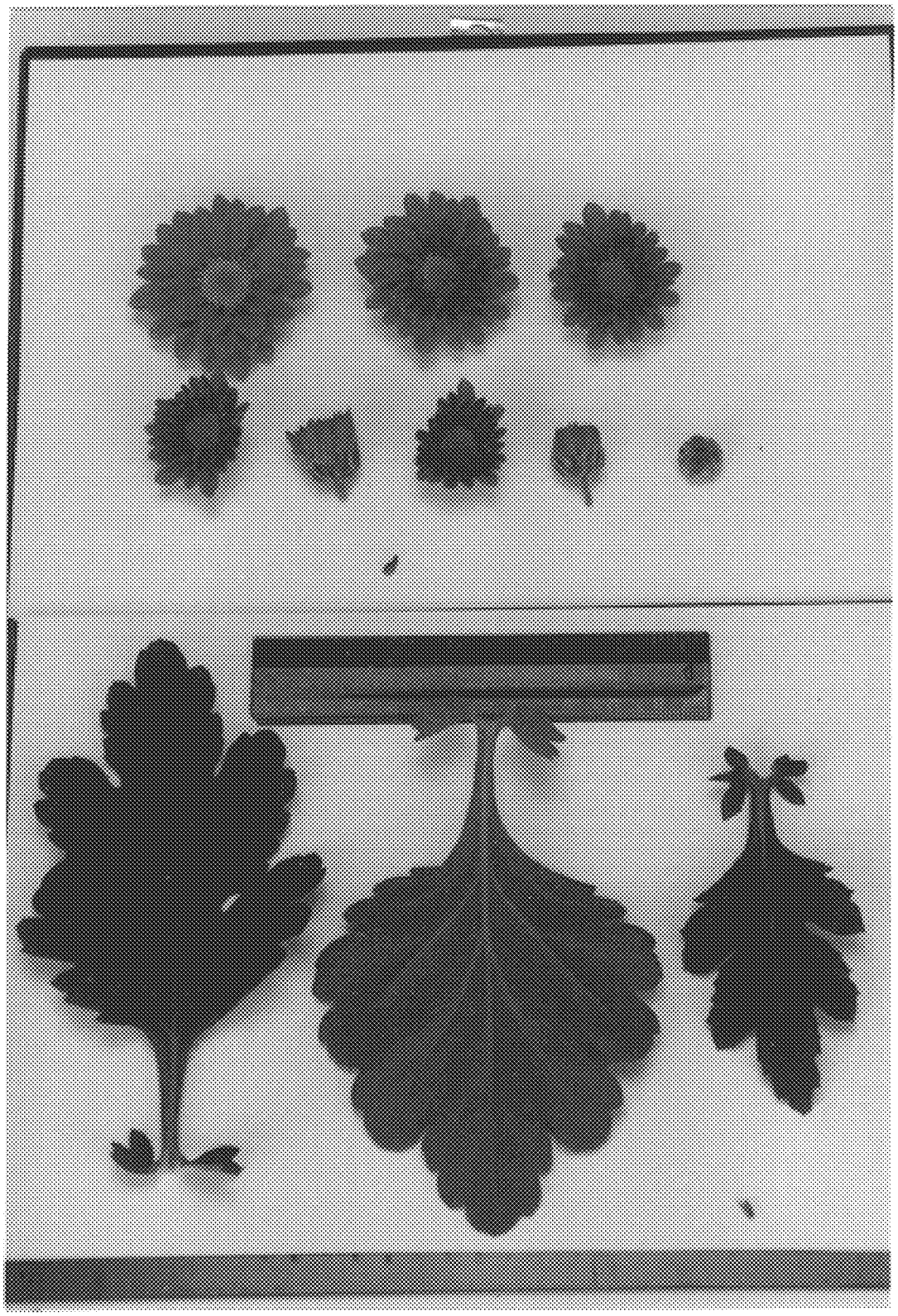
FIG. 2 shows the various stages of bloom and foliage of the new cultivar.

This new variety of chrysanthemum is of the botanical classification *Dendranthema grandiflora*. When grown in the vicinity of Ter Aar, Holland, it has a response time of approximately 8 weeks. This new variety produces small sized blooms with red ray florets and green-yellow disc florets having a 3 week performance (i.e., vase life of 21 days). This new variety of chrysanthemum has been found to retain its distinctive characteristics throughout successive propagations. However, the phenotype may vary significantly with variations in environment such as light intensity and temperature. To show the phenotype as described Red Refocus may be planted year round under greenhouse conditions in Holland.

The following is a description of the plant and characteristics that distinguish Red Refocus as a new and distinct variety. The color designations are taken from the plant itself. Accordingly, any discrepancies between the color designations and the colors depicted in the photographs are due to photographic tolerances.

| CULTIVAR | RED REFOCUS | Parent Cultivar REFOCUS |
|---|---|---|
| Bud | | |
| Size | small cross section + 1.0 cm, height ± 1.2 cm | medium, cross section ± 1.2 cm, height ± 1.2 cm |
| Outside Color | red 46B | red-purple 70A |
| Bloom | | |
| Size | small | small |
| Fully Expanded | 4–4½ cm | 4–4½ cm |
| Borne | upper portion single flower per peduncle, lower portion plural flower per peduncle | upper portion single flower per peduncle, lower portion plural flower per peduncle |
| Number of Blooms (per single stem) | average of 10 | average of 10 |
| Peduncle Lengths | near the top ±10 cm, near the middle 20 cm, near the bottom 20 cm. | near the top ±10 cm, near the middle 20 cm, near the bottom 20 cm. |
| Peduncle Lateral Shoot, Attachment | medium | medium |
| Peduncle Lateral Shoot, Angle | 30° | 30°–35° |
| Form | single (daisy) | single (daisy) |
| Performance (blooming period) | good, 21 days (18°–20° C.) | good, 21 days (18°–20° C.) |
| Color | | |
| Center of Flower/disc floret | yellow-green 144B at an early stage of inflorascence, mature yellow-orange 14B | yellow-green 15A at an early stage of inflorascence, mature yellow-orange 14B |
| Color of upper | red 45A | red-purple 71C |

-continued

| | | |
|---|---|---|
| surface of the majority of the ray-florets | | |
| Color of the lower surface of the majority of the ray-florets | red 45C | purple violet 80D |
| Tonality from Distance | a small red daisy | a small purple daisy |
| Discoloration | ray-florets to red 45C disc-floret to yellow-orange 14B | ray-florets to red-purple 72D disc-floret to yellow-orange 14B |
| Pollen | yellow-orange 14A | yellow-orange 14A |
| Ray florets | | |
| Texture | upperside smooth, underside smooth | upperside smooth, underside smooth |
| Number | 35–40 (2–3 rows) | 35–40 (2–3 rows) |
| Cross-section | concave | concave |
| Longitudinal axis of majority | straight | straight |
| Shape of tip | pointed | pointed |
| Fragrance | typical chrysanthemum | typical chrysanthemum |
| Disc Diameter | small to medium (1.0–1.2 cm) | small to medium (1.0–1.2 cm) |
| Reproductive Organs | | |
| Stamen (present in disc florets only) | yellow-green, thin, ± mm in length | yellow-green, thin, ± mm in length |
| Pollen | present, abundant | present, abundant |
| Styles (present in both ray and disc florets) | yellow-green, thin | yellow-green, thin |
| Style Length | ±4 mm | ±4 mm |
| Stigmas | yellow | yellow |
| Stigma Width | ±1 mm | ±1 mm |
| Ovaries | enclosed in calyx | enclosed in calyx |
| Plant | | |
| Form | spray mum meant for erect culture. Herbaceous | spray mum meant for erect culture. Herbaceous |
| Growth | short to medium | short to medium |
| Height | ±95–100 cm | ±95–100 cm |
| Stem Color | yellow-green 146B | yellow-green 146B |
| Stem Strength | strong | strong |
| Stem Brittleness | absent | present |
| Stem Anthocyanin Coloration | present | absent |
| Internodes | short (1.5–2.0 cm) | short (1.5–2.0 cm) |
| Flowering Response (photoperiodic controlled crop, no natural growing) | 8 weeks | 8 weeks |
| Foliage | | |
| Color | upperside yellow-green 147A underside yellow-green 147B | upperside yellow-green 147A underside yellow-green 147B |
| Size | length 10 cm; width 7 cm | length 9 cm; width 6 cm |
| Quantity (per single stem) | 28–32 | 28–32 |
| Shape | egg-shaped | egg-shaped |
| Texture | fleshy | fleshy |
| Ribs and Veins | both ribs and veins well developed | both ribs and veins well developed |
| Edge | crenated | crenated |
| Shape of Base of Sinus Between Lateral | round | round |

-continued

| | | |
|---|---|---|
| Lobes | | |
| Margin of Sinus Between Lateral Lobes | converging | converging |
| Shape of Base | truncated | rounded |
| Apex | mucronate | mucronate |
| Year of Discovery | 1993 | 1992 |

| CULTIVAR | PINK REFOCUS | WHITE REFOCUS |
|---|---|---|
| Bud | | |
| Size | medium, cross section ± 1.2 cm, height ±1.2 cm | medium cross section ± 1.5 cm, height ±1.0 cm |
| Outside Color | red-purple 58B | yellow-orange 20D |
| Bloom | | |
| Size | small | small |
| Fully Expanded | 4½–5 cm | 3½–4 cm |
| Borne | upper portion single flower per peduncle, lower portion plural flower per peduncle | upper portion single flower per peduncle, lower portion plural flower per peduncle |
| Number of Blooms (per single stem) | average of 10 | average of 10 |
| Peduncle Lengths | near the top ±10 cm, near the middle 20 cm, near the bottom 20 cm. | near the top ±10 cm, near the middle 20 cm, near the bottom 20 cm. |
| Peduncle Lateral Shoot, Attachment | medium to strong | medium |
| Peduncle Lateral Shoot, Angle | 30°–35° | 30°–35° |
| Form | single (daisy) | single (daisy) |
| Performance (blooming period) | good, 21 days (18°–20° C.) | good, 21 days (18°–20° C.) |
| Color | | |
| Center of Flower/disc floret | yellow-green 144B at an early stage of inflorescence, mature yellow-orange 14B | yellow-green 144A at an early stage of inflorescence, mature yellow-orange 14B |
| Color of upper surface of the majority of the ray-florets | near red-purple 58C | pure white 155D (but whiter) |
| Color of the lower surface of the majority of the ray-florets | red-purple 58C | pure white 155D (but whiter) |
| Tonality from Distance | a small pink/purple daisy | a clear white small daisy |
| Discoloration | ray-florets to red-purple 58D disc-floret to yellow-orange 14B | Ray florets none, disc florets to yellow-orange 14B |
| Pollen | Yellow-orange 14A | none |
| Ray florets | | |
| Texture | upperside smooth, underside smooth | upperside smooth, underside smooth |
| Number | 38–45 (3 rows) | 22–26 (2 rows) |
| Cross-section | concave | convex (no keels) |
| Longitudinal axis of majority | straight | reflexing |
| Shape of tip | pointed | rounded |
| Fragrance | typical chrysanthemum | typical chrysanthemum |
| Disc Diameter | mall to medium (1.0–1.2 cm) | small to medium (1.2–1.5 cm) |
| Reproductive Organs | | |
| Stamen (present in disc florets only) | yellow-green, thin, ±4 mm in length | yellow-green, thin, ±4 mm in length |
| Pollen | present, abundant | none |

-continued

| | | |
|---|---|---|
| Styles (present both ray and disc florets) | yellow-green, thin | yellow-green, thin |
| Style Length | ±4 mm | ±4 mm |
| Stigmas | yellow | yellow |
| Stigma Width | ±1 mm | ±1 mm |
| Ovaries | enclosed in calyx | enclosed in calyx |
| Plant | | |
| Form | spray mum meant for erect culture. Herbaceous | spray mum meant for erect culture. Herbaceous |
| Growth | short to medium | short to medium |
| Height | ±100–105 cm | ±100–105 cm |
| Stem Color | yellow-green 146B | yellow-green 147B |
| Stem Strength | strong | strong |
| Stem Brittle-ness | absent | present |
| Stem Anthocyanin Coloration | present | present |
| Internodes | short (1.5–2.0 cm) | short (1.5–2.0 cm) |
| Flowering Response (photoperiodic controlled crop, no natural growing) | 8 weeks | 8 weeks |

-continued

| | | |
|---|---|---|
| Foliage | | |
| Color | upperside yellow-green 147A<br>underside yellow-green 147B | upperside yellow-green 147A<br>underside yellow-green 147B |
| Size | length 9 cm; width 6 cm | length 9 cm; width 6 cm |
| Quantity (per single stem) | 28–32 | 30–35 |
| Shape | egg-shaped | egg-shaped |
| Texture | fleshy | fleshy |
| Ribs and Veins | both ribs and veins well developed | both ribs and veins well developed |
| Edge | crenated | crenated |
| Shape of Base of Sinus Between Lateral Lobes | round | round |
| Margin of Sinus Between Lateral Lobes | converging | converging |
| Shape of Base | obtuse | truncated |
| Apex | cuspidate | mucronate |
| Year of Discovery | 1993 | 1995 |

I claim:

1. A new and distinct variety of chrysanthemum plant as described and illustrated.

* * * * *